(12) United States Patent (10) Patent No.: US 9,089,152 B2
Brodkorb et al. (45) Date of Patent: Jul. 28, 2015

(54) METHOD OF PRODUCING MICROBEADS

(75) Inventors: Andre Brodkorb, Middleton (IE); Sinead Doherty, Cork (IE)

(73) Assignee: TEAGASC—Agriculture and Food Development Authority, Oak Park, Carlow (IE)

( * ) Notice: Subject to any disclaimer, the term of this patent is extended or adjusted under 35 U.S.C. 154(b) by 43 days.

(21) Appl. No.: 13/264,381

(22) PCT Filed: Apr. 13, 2010

(86) PCT No.: PCT/EP2010/054846
§ 371 (c)(1),
(2), (4) Date: Mar. 1, 2012

(87) PCT Pub. No.: WO2010/119041
PCT Pub. Date: Oct. 21, 2010

(65) Prior Publication Data
US 2012/0156252 A1    Jun. 21, 2012

Related U.S. Application Data

(60) Provisional application No. 61/168,746, filed on Apr. 13, 2009.

(51) Int. Cl.
*A23L 1/00*    (2006.01)
*A23L 1/052*    (2006.01)
(Continued)

(52) U.S. Cl.
CPC ............... *A23L 1/0029* (2013.01); *A23L 1/052* (2013.01); *A23L 1/2115* (2013.01); *A23L 1/3014* (2013.01); *A23L 1/3056* (2013.01); *A23P 1/04* (2013.01); *B01J 13/0065* (2013.01); *A23V 2002/00* (2013.01)

(58) Field of Classification Search
None
See application file for complete search history.

(56) References Cited

U.S. PATENT DOCUMENTS 4,217,370 A    8/1980 Procter et al.
2008/0044481 A1*    2/2008 Harel ........................... 424/490

FOREIGN PATENT DOCUMENTS

EP    1234507    * 2/2001    ................ A23J 1/20
WO    WO 97/48288    12/1997
(Continued)

OTHER PUBLICATIONS

Bipro Whey Protein Isolate; Accessed Mar. 25, 2013, pp. 1-2.*
(Continued)

*Primary Examiner* — Rachael E Bredefeld
(74) *Attorney, Agent, or Firm* — Cotman IP Law Group, PLC

(57) ABSTRACT

A method for producing microbeads comprising an active component encapsulated within a gelled polymer matrix comprises the steps of providing a suspension of denatured whey protein and an active component, treating the suspension to generate microbeads, and immediately curing the microbeads by acidification. The microbeads are discrete droplets of gelled whey protein having an average diameter in the micron range (for example, from 80 to 500 microns) and which, suitably have a generally spherical shape. The microbeads are capable of surviving passage through the stomach, and delivering the encapsulated active agent in the instestine. Ex-vivo and in-vivo data shows that active agent encapsulated within microbeads retains its functionality upon delivery to the intestine, and that coating of the microcapsules allows targeted delivery of the active agent to the distal part of the intestine.

14 Claims, 12 Drawing Sheets

(51) Int. Cl.
*A23P 1/04* (2006.01)
*A61K 9/16* (2006.01)
*B01J 13/02* (2006.01)
*B01J 13/04* (2006.01)
*B01J 13/22* (2006.01)
*A23L 1/211* (2006.01)
*A23L 1/30* (2006.01)
*A23L 1/305* (2006.01)
*B01J 13/00* (2006.01)

(56) References Cited

FOREIGN PATENT DOCUMENTS

| WO | WO03/106014 | * 12/2003 | ............... B01J 13/10 |
|----|-------------|-----------|---------------------------|
| WO | WO 2005072709 | 8/2006 | |

OTHER PUBLICATIONS

Ainsley Reid et al. "MIcroentrapment of probiotic bacteria in a Ca(2+)-induced whey protein gel and effects on their viability in a dynamic gastro-intestinal mode" Journal of Microencapsulation, Taylor and Francis, Basingstoke, GB, vol. 22, No. 6, Sep. 1, 2006; pp. 603-619.

Arnaud Picot, "Encapsulation of bifdobacteria in whey protein-based microcapsules and survival in simulated gastrointestinal conditions and in yoghurt" INternaional Dairy Journal, vol. 14, No. 6, 2004, pp. 505-515.

A.Ainsley Reid et al. "Survivial in Food Systems of *Lactobacillus rhamnosus* R011 Microentrapped in Whey Protein Gel Particles" Journal of Food Science, vol. 72, No. 1, 2007, pp. M31-M37.

* cited by examiner

METHOD OF PRODUCING MICROBEADS

CROSS-REFERENCE TO RELATED APPLICATIONS

This application is the National Stage of International Application No. PCT/EP2010/054846 filed Apr. 13, 2010, which claims the priority of U.S. Provisional Application No. 61/168,746, filed on Apr. 13, 2009. The contents of both applications are hereby incorporated by reference in their entirety.

INTRODUCTION

The invention relates to a method for producing microbeads comprising an active component encapsulated within a gelled polymer matrix. In particular, the invention relates to a method for producing microbeads comprising sensitive components such as probiotic bacteria encapsulated within a gelled polymer matrix. The invention also relates to microbeads comprising an active component encapsulated within a polymer matrix.

BACKGROUND TO THE INVENTION

The method of using whey proteins for creating whey protein gel-beads is not novel. Ainsley Reid et al., 2005 (Ainsley Reid, A., J. C. Vuillemard, M. Britten, Y. Arcand, E. Farnworth, and C. P. Champagne. 2005. Microentrapment of probiotic bacteria in a Ca ($^{2+}$)-induced whey protein gel and effects on their viability in a dynamic gastro-intestinal model. Journal of Microencapsulation 22:603-19.) described a method that involves the production of simple droplet beads using pipettes/syringes followed by a gelation step. This method produces very large bead gels that are mostly unsuitable for food preparation.

Rosenberg, 1994 (Rosenberg, M. 1993. Whey proteins as microencapsulating agents—Microencapsulation of anhydrous milkfat—Structure evaluation Food Structure 12:31. or Rosenberg, M. a. L., S. L. 1993. Microstructure of whey protein/anhydrous milkfat emulsions. Food Structure 12:267-274) described the emulsification of denatured whey protein mixture by high pressure homogenisation or high shear, followed by internal gelation and subsequent separation of gel and oil phase. The major disadvantages of this method is that use of high pressure/high shear necessary for the formation of the micro-beads can cause significant damage to the active component the micro-bead is encasing. Also, the presence of an oil phase and its removal through the use of detergents can also be damaging to some active components, like probiotic bacteria.

STATEMENTS OF INVENTION

The Applicant has surprisingly discovered that microbeads derived from heat-denatured whey protein immediately gelled and cured in an acidification bath, form stable, robust and ideally spherical microbeads capable of encapsulating sensitive components and protecting the components from the low pH environment of the stomach, while also being capable of controlled release of the components in the more neutral pH conditions of the small intestine.

Accordingly, in a first aspect, the invention relates to a method for producing microbeads comprising an active component encapsulated within a gelled polymer matrix, the method comprising the steps of providing a suspension of denatured whey protein and an active component, treating the suspension to generate microbeads, and immediately curing the microbeads by acidification.

In this specification, the term "microbeads" should be understood to mean discrete droplets of gelled whey protein having an average diameter in the micron range (for example, from 80 to 500 microns) and which suitably have a generally spherical shape.

The pH of the acidification step should be close to the pI of the β-lactoglobulin in the whey protein mixture. Preferably, the acidification step is carried out at a pH of from 4.0 to 4.9, more preferably a pH of from 4.1 to 4.8, 4.2 to 4.7, 4.3 to 4.7, preferably a pH of about 4.5 to 4.7, and ideally a pH of about 4.6.

Ideally, the whey protein is a whey protein isolate. However, other types of whey protein fractions may also be employed in the process of the invention, for example whey protein hydrolysate or whey protein concentrates.

Typically, the microbeads are cured in an acidification bath containing an acidic curing solution, suitably an acetate solution, although other acids may be employed. The parameters of the acidification bath are chosen to ensure instantaneous gelation of the microbeads. That is to say that the microbeads gel (i.e. harden) immediately upon contact with the acid curing solution. It has been surprisingly found that if the parameters of the acidification bath are such that instantaneous gelation does not occur, the resultant micro-beads have irregular, non-homogenous, shapes. In contrast, when instantaneous gelation does occur, microbeads having a spherical, homogenous shape are produced. The parameters required to achieve instantaneous gelation depend on the characteristics of the whey protein, including the degree of denaturation, and the type and amount of active component. Generally, the parameters of the acid curing solution that are varied are pH, acid concentration, and temperature. In the example provided below, in which a 9% WPI suspension having about 80% β-lactoglobulin (having a degree of denaturation of about 95%) is employed, and in which the active component is a probiotic bacteria, the pH of the acidic solution is 4.2 to 4.7, the acid concentration of 0.3 to 0.6 M, and the temperature of the acidic solution is from 30° C. to 40° C. Suitably, the pH of the acidic solution is 4.5 to 4.7, the acid concentration of 0.4 M to 0.6 M, and the temperature of the acidic solution is from 34° C. to 48° C. Ideally, the pH of the acidic solution is about 4.6, the acid concentration is about 0.5 M, and the temperature of the acidic solution if from 35° C. to 37° C.

Typically, the acidic curing solution comprises a surfactant to prevent or inhibit agglomeration of the formed microbeads. Suitably, the surfactant is a polysorbate surfactant, ideally Tween 20.

Suitably, the formed microbeads are subject to an extended curing period in the acidification bath, for a period of at least 15 minutes (after gelation), and preferably for a period of at least 20 minutes. In a preferred embodiment of the invention, the formed microbeads are cured for a period of time from 20 to 180, 20 to 120, or 20 to 60 minutes. Ideally, the acidic curing solution is agitated during the curing process.

Generally, the method involves an initial step of denaturing the whey protein. Ideally, the whey protein is heat-denatured, although other methods of denaturation are also applicable, for example pressure-induced denaturation. In a preferred embodiment, the whey protein is heat-denatured at a temperature of from 75° C. to 80° C., suitably for a period of between 30 minutes and 50 minutes. Typically, the whey protein is agitated during heat-denaturation.

Suitably, the concentration of the whey protein (prior to the addition of the sensitive component) is from 5 to 15%, preferably from 7 to 12%, and ideally from 9 to 11% (w/v).

Typically, the denatured whey protein is in the form of a soluble suspension (prior to addition of the active component), in which partial gelation of the β-lactoglobulin has produced suspended protein agglomerates. Typically, the suspension is subject to a filtration process, generally prior to addition of the active component. In one preferred embodiment, the suspension is passed through a plurality of filters having a gradually decreasing pore size. Ideally, the final filter has a sub-micron pore size, for example 0.1 to 0.9 microns.

Ideally, the whey protein employed in the process of the invention has a β-lactoglobulin content of at least 30%, 40%, 50%, 60%, 70% or 80% (w/w). Typically, the β-lactoglobulin has a degree of denaturation of at least 60%, 70%, 80%, 90% or 95%.

Various methods will be apparent to the skilled person for generating microbeads, for example prilling and spraying. A preferred method of producing the microbeads is a vibrating nozzle technique, in which the suspension is sprayed through a nozzle and laminar break-up of the sprayed jet is induced by applying a sinusoidal frequency with defined amplitude to the spray nozzle. Examples of vibrating nozzle machines are the ENCAPSULATOR (Inotech, Switzerland) and a machine produced by Nisco Engineering AG, or equivalent scale-up version such as those produced by Brace GmbH or Capsulæ and the like.

Typically, the spray nozzle has an aperture of between 100 and 600 microns, preferably between 100 and 200 microns, suitably 140 and 160 microns, and ideally about 150 microns.

Suitably, the frequency of operation of the vibrating nozzle is from 900 to 3000 Hz. Generally, the electrostatic potential between nozzle and acidification bath is 0.85 to 1.3 V. Suitably, the amplitude is from 4.7 kV to 7 kV. Typically, the falling distance (from the nozzle to the acidification bath) is less than 50 cm, preferably less than 40 cm, suitably between 20 and 40 cm, preferably between 25 and 35 cm, and ideally about 30 cm. The flow rate of suspension (passing through the nozzle) is typically from 3.0 to 10 ml/min; an ideal flow rate is dependent upon the nozzle size utilized within the process.

In one embodiment, the process involves a step of detecting the size of the initial microbeads generated, comparing the detected size of the microbeads with a predetermined desired size, and wherein the detected size differs significantly from the predetermined desired size, the microbeads are diverted away from the acidification bath until the detected size correlates with the predetermined desired size.

In one embodiment of the invention, the active component is a suspension of cells, typically bacterial cells, ideally a probiotic bacteria cell suspension. Suitably, the concentration of cells in the suspension is from $1\times10^7$ to $5\times10^{11}$ cfu/ml, preferably from $1\times10^8$ to $5\times10^{10}$ cfu/ml, ideally from $1\times10^9$ to $7\times10^{10}$ cfu/ml.

In one aspect, the methods of the invention do not involve exposing the microbeads to high pressure or high shear (i.e. homogenisation). This avoids damage to any components that are sensitive to pressure or shear such as, for example, prokaryotic or eukaryotic cells.

The invention also relates to a preparation of microbeads in which each microbead (i.e. all or most of the microbeads) comprises an active component dispersed within a gelled denatured whey protein matrix, and wherein at least 50%, 60%, 70%, 80% or 90% of the microbeads in the preparation have a diameter in a 80 to 500μ range.

Typically, at least 90% of the microbeads in the preparation are capable of surviving intact in fresh ex-vivo porcine gastric juice of pH 2.0 for at least three hours at 37° C. under agitation at 150 rpm (employing the methods as described below).

Ideally, substantially all of the microbeads in the preparation are capable of surviving intact in fresh ex-vivo porcine gastric juice of pH 2.0 for at least three hours at 37° C. under agitation at 150 rpm (employing the methods as described below).

Typically, the whey protein matrix comprises at least 30%, 40%, 50%, 60%, 70%, or 80% β-lactoglobulin (w/w). Suitably, the β-lactoglobulin has a degree of denaturation of at least 50%, 60%, 70%, 80%, 90% or 95%. In a preferred embodiment of the invention, the whey protein comprises at least 70% β-lactoglobulin having a degree of denaturation of at least 90%.

Ideally, the whey protein is whey protein isolate (WPI) or whey protein concentrate (WPC).

Preferably, a majority of the microbeads in the preparation are spherical.

Suitably, the active component is homogenously dispersed within the polymer matrix.

In a preferred embodiment, at least 90% of the microbeads in the preparation have a diameter from 200 microns to 300 microns.

In a preferred embodiment of the invention, the active agent is a cell, preferably a probiotic cell preparation. Thus, the microbead preparation of the invention may be used to safely transport probiotic cells through the stomach and bile salt domain (where the cells are protected by the microbeads from harsh gastric conditions) for delivery of cells to the distal intestinal tract.

The invention also relates to a food product or beverage comprising a microbead preparation of the invention. Various types of food products are envisaged including dairy products (for example, yoghurt, milk, cheese, etc) and acidic fruit products.

The invention also relates to a vehicle capable of delivering an active agent to a lower intestine of a subject while protecting the active agent during passage through the stomach of the subject, the vehicle comprising a microbead preparation according to the invention. Thus, as explained above, the microbeads have a net positive charge and are substantially resistant to the low pH conditions of the stomach and, as such, protect the encapsulated active agents entrapped within the microbead. However, as the microbeads transit through the gut to the intestine, the pH of the environment increases to above the pI of the whey protein, which causes the microbead gels to weaken, allowing endogenous proteolytic enzymes disintegrate the gel and release the entrapped active agents.

The invention also relates to a method of delivering an active agent to a lower intestine of a subject and protecting the active agent during passage through a stomach of the subject, and in which the active agent is susceptible to degradation in the acidic conditions of the stomach, the method comprising a step of orally administering a preparation of microbeads according to the invention to the subject.

The invention also provides a method for producing coated microbeads comprising the steps of producing microbeads according to a method of the invention, and re-suspending the microbeads in a solution of anionic polysaccharide having a pH of 4.6 or less for a period of at least 10, 30, 60, 90, 120, 180 minutes. In this specification, the term "anionic polysaccharide" should be understood to mean a polysaccharide that has a net negative charge when dissolved or solubilised in a solution having a pH of 4.6 or less. Examples of suitable anionic polysaccharides include pectins, alginates, carrageenans, and acacia gums (for example, Apple Pectin, Citrus Pectin, Sodium Alginate, Kappa carrageenan, iota carrageenan, and gum acacia).

Suitably, when the microbeads are coated with alginate, they are cured after the coating step, for example, cured in a solution of calcium chloride (0.1-0.5 M, typically about 0.2 M).

The invention also relates to a preparation of coated microbeads in which each coated microbead (i.e. all or most of the coated microbeads) comprises a microbead coated with a layer of anionic polysaccharide, and wherein the microbead comprises an active component dispersed within a gelled denatured whey protein matrix.

Typically, at least 50%, 60%, 70%, 80% or 90% of the microbeads in the preparation have a diameter of from 80 to 500μ.

Suitably, at least 90% and ideally 100% of the coated microbeads in the preparation are capable of (a) surviving intact in fresh ex-vivo porcine gastric juice of pH 1.8 for at least three hours at 37° C. under agitation at 150 rpm, and, optionally, (b) rupturing in fresh ex-vivo porcine jejunum juice of pH 6.59 within one hour at 37° C. under agitation at 150 rpm.

Suitably, at least 90% and ideally 100% of the coated microbeads in the preparation are capable of (a) surviving intact in fresh ex-vivo porcine gastric juice of pH 1.8 for at least three hours at 37° C. under agitation at 150 rpm, and (b) rupturing in fresh ex-vivo porcine intestinal juice of pH 6.59 within 40 minutes at 37° C. under agitation at 150 rpm.

Generally, at least 90% or 100% of the coated microbeads in the preparation are capable of surviving intact in fresh ex-vivo porcine gastric juice of pH 2.4 for at least two hours at 37° C. under agitation at 150 rpm, and wherein at least 50%, 60%, 70%, 80%, or 90% of the coated microbeads rupture in fresh ex-vivo porcine jejunum juice of pH 6.59 within 40 minutes at 37° C. under agitation at 150 rpm.

Typically, the anionic polysaccharide is selected from the group consisting of: pectin; alginate; carrageenan; and acacia. Preferably, the anionic polysaccharide is selected from the group consisting of Apple Pectin, Citrus Pectin, Sodium Alginate, Kappa carrageenan, iota carrageenan, and gum acacia.

Typically, the whey protein matrix comprises at least 30%, 40%, 50%, 60%, 70%, or 80% β-lactoglobulin (w/w). Suitably, the β-lactoglobulin has a degree of denaturation of at least 50%, 60%, 70%, 80%, 90% or 95%. In a preferred embodiment of the invention, the whey protein comprises at least 70% β-lactoglobulin having a degree of denaturation of at least 90%.

Ideally, the whey protein is whey protein isolate (WPI).

Preferably, a majority of the coated microbeads in the preparation are spherical.

Suitably, the active component is homogenously dispersed within the polymer matrix.

In a preferred embodiment, at least 90% of the coated microbeads in the preparation have a diameter of from 200 microns to 300 microns.

In a preferred embodiment of the invention, the active agent is a cell, preferably a probiotic cell preparation.

The invention also relates to a dairy product comprising a preparation of coated microbeads according to the invention.

The invention also relates to a vehicle capable of delivering an active agent to a lower intestine of a subject while protecting the active agent during passage through the stomach of the subject, the vehicle comprising a coated microbead preparation according to the invention.

The invention also relates to a method of delivering (i.e. releasing) an active agent to a distal intestinal region of a subject and protecting the active agent during passage through a stomach and proximal intestinal region of the subject, and in which the active agent is susceptible to degradation in the acidic conditions of the stomach, the method comprising a step of orally administering to the subject a preparation of coated microbeads according to the invention. Typically, the active agent is a cell, ideally a probiotic bacterial preparation.

As indicated above, the term whey protein should generally be understood as meaning a whey protein fraction having at least 30% β-lacoglobulin, for example various types of whey protein concentrates. Ideally, the whey protein is a whey protein isolate (WPI) suitably having at least 70% or 80% beta-lactoglobulin. The active component for example maybe a component that is sensitive to processing conditions, in-vivo conditions, or storage conditions, for example, probiotic bacteria which are sensitive to damage by acidic gastric-transit conditions, or by high sheer or high pressure forces being exerted during processing. Thus, the active component may be sensitive to pH, enzymes (i.e. protease enzymes), high pressure, high shear, and temperature abuse during storage. In one particularly preferred embodiment of the invention, the active component is a cell, typically a bacterial cell, and ideally a probiotic cell. Such cells are sensitive to low pH conditions, such as would be encountered in the stomach, and as such need to be shielded from gastric pH and bile salt environments. Probiotic bacteria, and indeed other types of cells, are also sensitive to high shear or high pressure, such as are employed in conventional methods of generating micron-sized polymer beads. Other types of active components which may be encapsulated in the microbeads of the invention include enzymes, starter bacteria, cell extracts, proteins and polypeptides, sugars and sugar derivatives, nucleic acids and nucleic acid constructs, pharmaceutically-active agents, imaging dyes and ligands, antibodies and antibody fragments, pytochemicals and the like.

The invention also relates to a food product, especially a dairy product, comprising microbeads (coated or otherwise), or a preparation of microbeads (coated or otherwise), according to the invention.

The Applicant has surprisingly discovered that the microbeads of the invention are capable of selectively removing phytochemical compounds from liquids. As an example the Applicant has successfully removed a large proportion of anthocyanin compounds from cranberry juice. These compounds become part of the payload of the microbeads, and can be successfully delivered through the stomach and released in the small intestine. The invention thus also relates to a method of removing a phytochemical fraction/product from a liquid comprising a step of admixing a preparation of microbeads according to the invention with the liquid to allow the microbeads adsorb a phytochemical fraction from the liquid. Examples of phytochemical compounds are polyphenolic compounds (i.e. anthocyanins), fat soluble vitamins, and the like.

Thus, the invention also relates to a preparation of bioactive microbeads comprising microbeads according to the present invention having one or more phytochemical compounds adsorbed onto an outer surface of the microbeads. The method also relates to a method of delivering bioactive phytochemical compounds to the lower intestine of a subject comprising a step of orally administering a preparation of bioactive microbeads to the subject. The invention also relates to a method of making bioactive microbeads comprising a step of admixing a preparation of microbeads according to the invention with a phytochemical-containing fluid for a sufficient period of time to allow at least a portion of the phytochemical fraction of the fluid adsorb to the microbeads and, optionally, removing the bioactive microbeads from the fluid.

The invention also relates to a food product comprising a preparation of bioactive microbeads according to the invention. The food product may be, for example, a dairy product such as a milk drink, a yoghurt or the like, or a fruit-based food or drink.

The invention also relates to a method of debittering a product (i.e. reducing the bitter taste of the product) for example a beverage product, for example a fruit-based beverage, of the type comprising phytochemical bitter-tasting compounds, the method comprising a step of admixing a preparation of microbeads according to the invention with the product for a sufficient period of time to allow at least a portion of the phytochemical bitter-tasting compounds of the product adsorb to the microbeads, and removing the microbeads and adsorbed bitter-tasting compounds from the fluid.

BRIEF DESCRIPTION OF THE FIGURES

FIGS. 6*c* and 6*d* illustrate bead homogeneity and probiotic cell distribution, respectively.

DETAILED DESCRIPTION OF THE INVENTION

Methods

Chemicals

BiPro, a commercial whey protein isolate (WPI) was obtained from Davisco Foods International Inc., (Le Sueur, Minn., U.S.A.). WPI native β-lactoglobulin (β-Lg) and α-lactalbumin (α-La) content were analyzed by reverse phase-HPLC and estimated at 82% and 16%, respectively. Sodium acetate was obtained from Sigma Chemicals Co. (Basingstoke, Hampshire, UK). Tween-20 and acetic acid were obtained from BDH (Alchem Chemicals Ltd., Little Island, Co. Cork, Ireland). The chemical products used in high performance liquid chromatography (HPLC) were acetonitrile (ACN) and trifluoroacetic acid (TFA), both HPLC grade. Highly purified water (Milli-Q PLUS, Millipore Corporation) was used in all cases for dispersion of samples, culture mediums and buffer solutions.

Probiotic Cultures & Cell Suspensions

In-Vitro and Ex-Vivo Data

The probiotic strain *Lactobacillus rhamnosus* GG (ATCC 53103, *L. rhamnosus* GG, Valio Ltd., Finland), was procured from University College Cork, under a restricted materials transfer agreement. Harvested cells were stored as stock solutions in de Man Rogosa Sharpe (MRS) broth (Oxoid Ltd., Hampshire, U.K.) (REFERENCE: De Man, J. C., Rogosa, M. and Sharpe, M. E. 1960. A medium for cultivation of *lactobacilli*. Journal of Applied Bacteriology 23:130-135. containing 50% (v/v) aqueous glycerol at −20° C. All tests were performed using subcultures from the same frozen stock, which was routinely checked for purity. Prior to assay, *L. rhamnosus* GG was serially transferred three times in MRS broth (Oxoid Ltd., Hampshire, U.K.) and incubated anaerobically at 37° C. for 24 hour (Merck, Darmstadt, Germany). Bacteria destined for encapsulation were propagated from 1% (v/v) inoculums for 19 hour at 37° C. under anaerobic conditions. The probiotic biomass in early stationary phase ($10^9$ cfu/mL) was harvested by centrifugation at 5,200×g for 10 minutes at 4° C. (Sorvall, RC-5C Plus, Sorvall Products, Stevenage, Herts, UK), washed, filter-sterilized and resuspended in sterile phosphate-buffered saline (Sigma Chemical CO, St Louis, U.S.A.). Fresh cells suspensions prepared for each experiment were enumerated by pour plating in MRS agar (anaerobic incubation at 37° C. for 48 hour) and subsequently used either directly in the assay (free-cell condition) or employed within the microencapsulation process.

Microbead Matrix & Curing Media

WPI was hydrated in sterile water (11% w/v) for 16 h at 4° C. under slight agitation (180 rpm) in order to permit good protein hydration. WPI solution was adjusted to pH 7 with 100 mM HCl and filtered through 0.45 μm (Millex, HVLP, Millipore Corp., Bedford, Mass.) to remove traces of undissolved material. The protein dispersion was subsequently heated at 78-80° C. for 30-45 minutes under agitation (to promote protein polymerization. The suspension of reactive WPI aggregates was subsequently cooled on ice, stored at 4° C. overnight.

Figure 3:
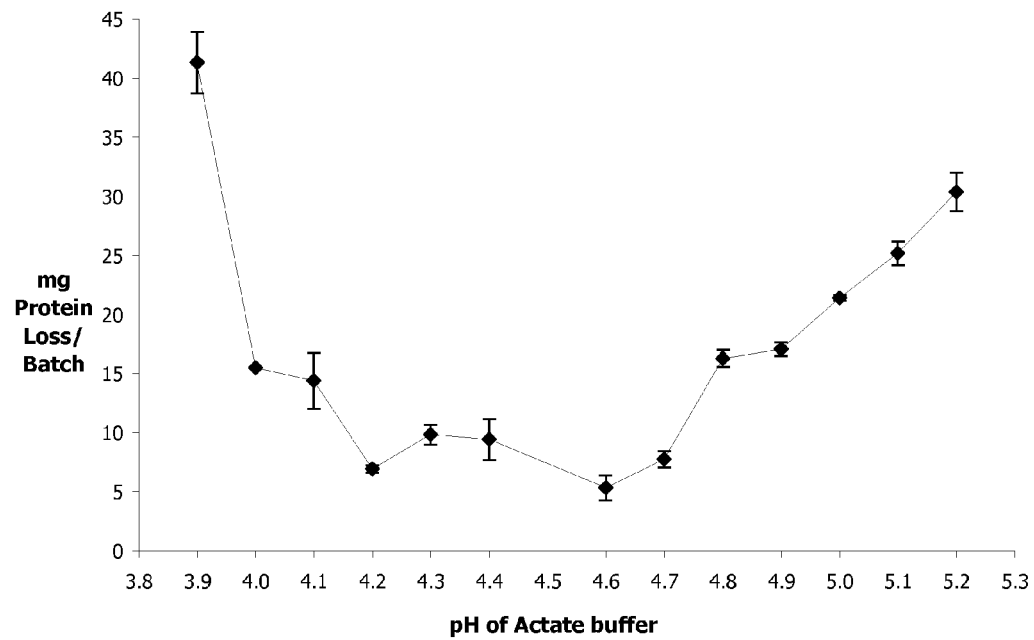
FIG. 3: The protein leakage expressed as protein loss (mg)/ 250 mL of acetate buffer during micro-bead formation as a function of acetate pH. Protein concentration was determined according to the Bradford assay.
Figure 4:
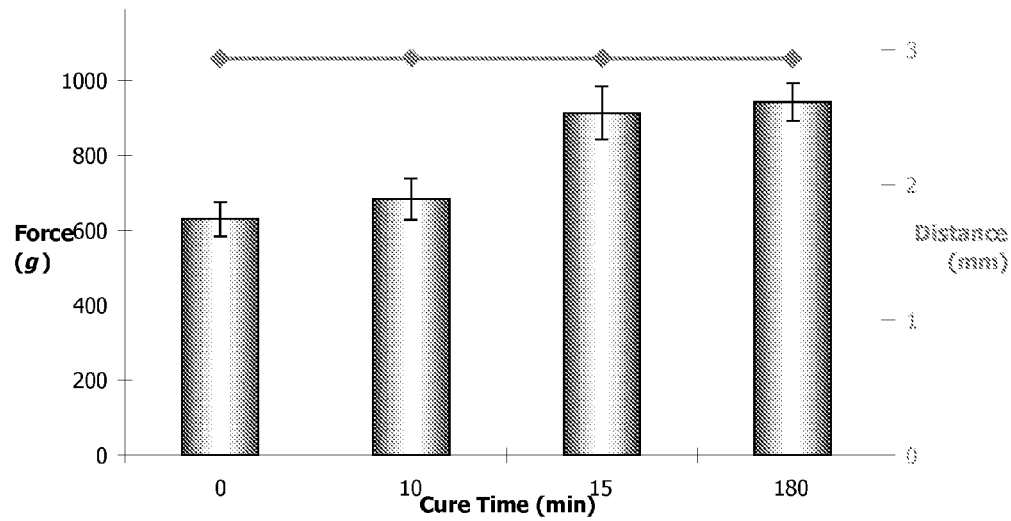
FIG. 4: Micro-bead strength as a function of curing time (0-180 minutes) in acetate buffer. Compression distance (♦) remains constant throughout the assay, indicating the presence of a monolayer micro-bead sample.
Figure 5:
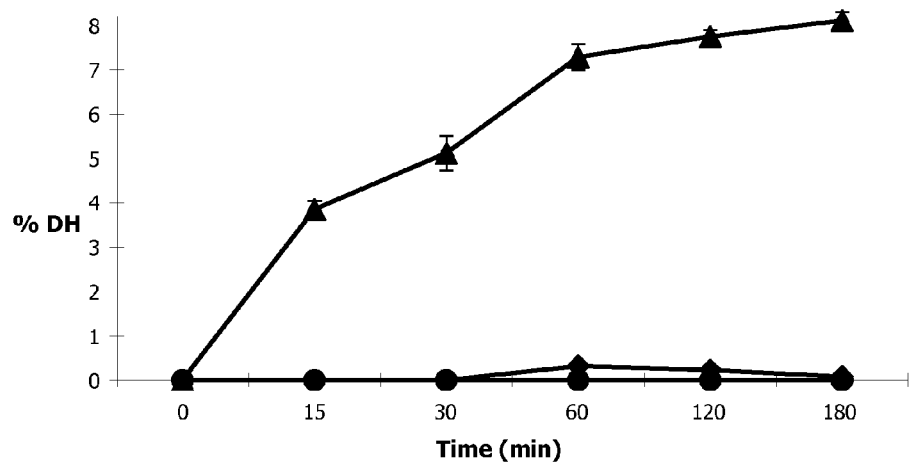
FIG. 5: Degree of hydrolysis of whey protein micro-beads as a function of digestive media at 37° C. HCl pH 1.8 (♦), Intestinal juice pH 7.6 (▲) and phosphate buffered saline (PBS) pH 7.6 (●) were incubated for 180 minutes at 200 rpm. Degree of hydrolysis was determined according to the OPA assay.
Figure 6:
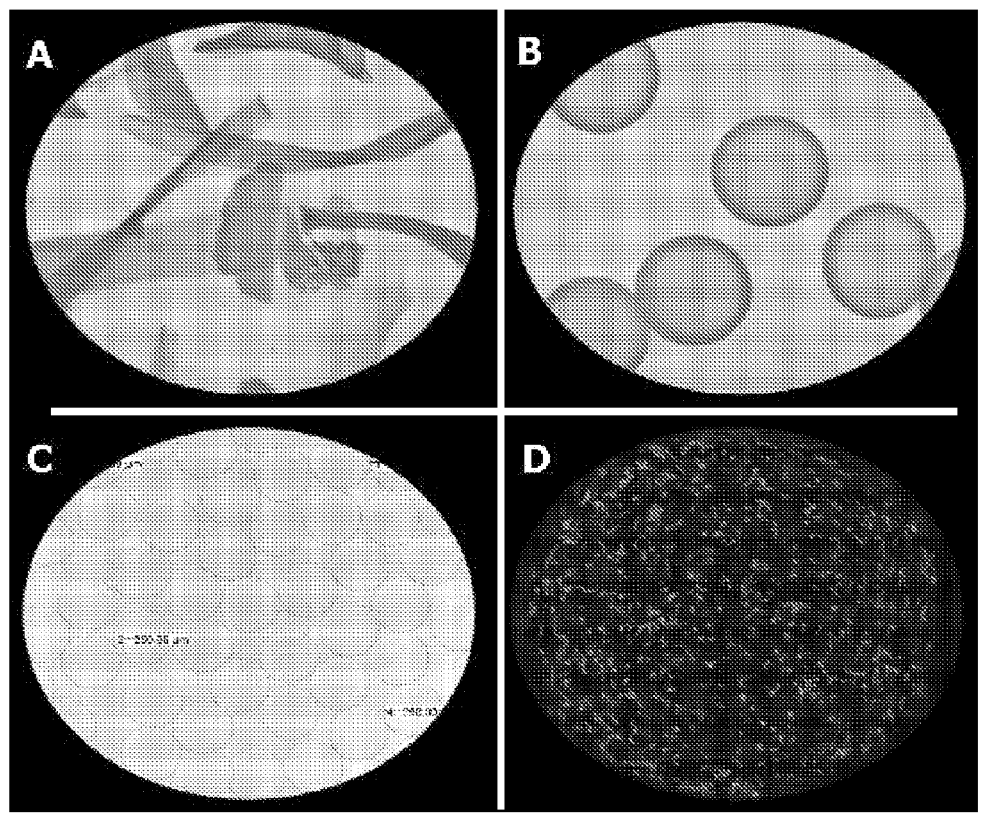
FIG. 6: Light microscope images of whey protein microbeads far from the isoelectric point (pI) of whey proteins (A), close to pI (B).
Figure 7:
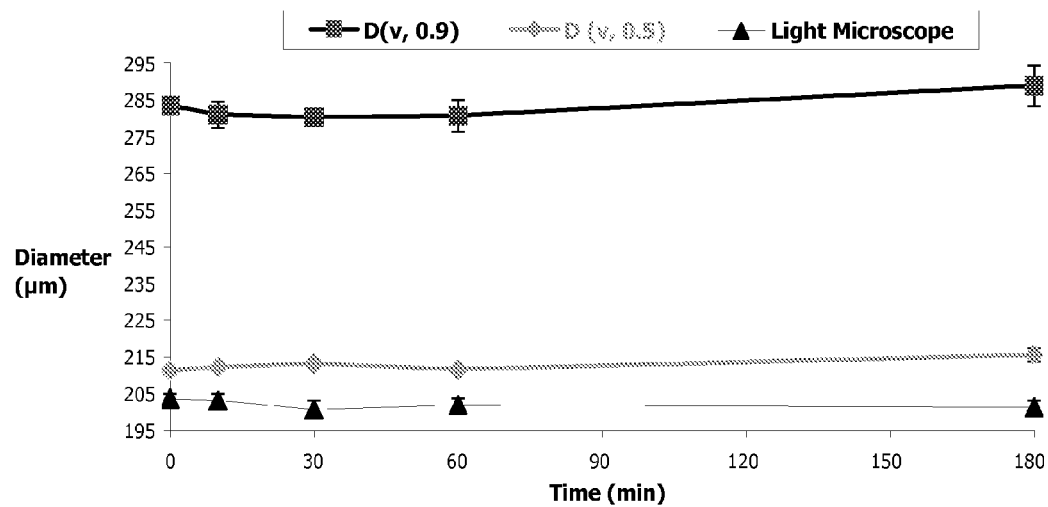
FIG. 7: Size Distribution of whey protein micro-beads as a function of curing time at an acetate pH close to the pI of WPI as measured by laser diffractometry and light microsopy. D (v, 0.9) represents 90% if micro-beads with a diameter below 282 μm and D (v, 0.5) represents 50% if micro-beads with a diameter below 212 um; however, light microscopy measured an average diameter of 202.21 μm±0.04 μm.
Figure 8:
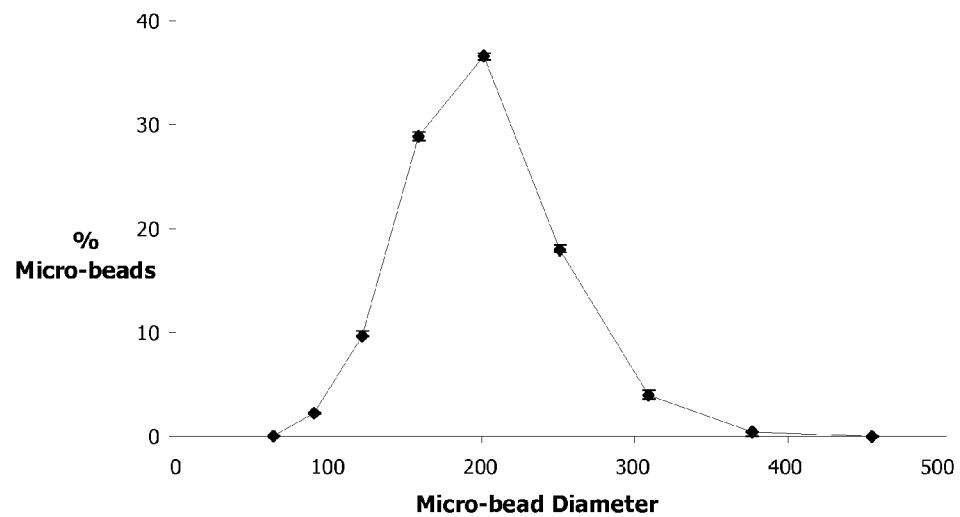
FIG. 8: Particle size distribution of whey protein microbeads at an acetate pH close to the pI of WPI (average size, 216.36±1.48 μm; size at peak 201.68±0.43 μm) using laser diffractometry.
Figure 9:
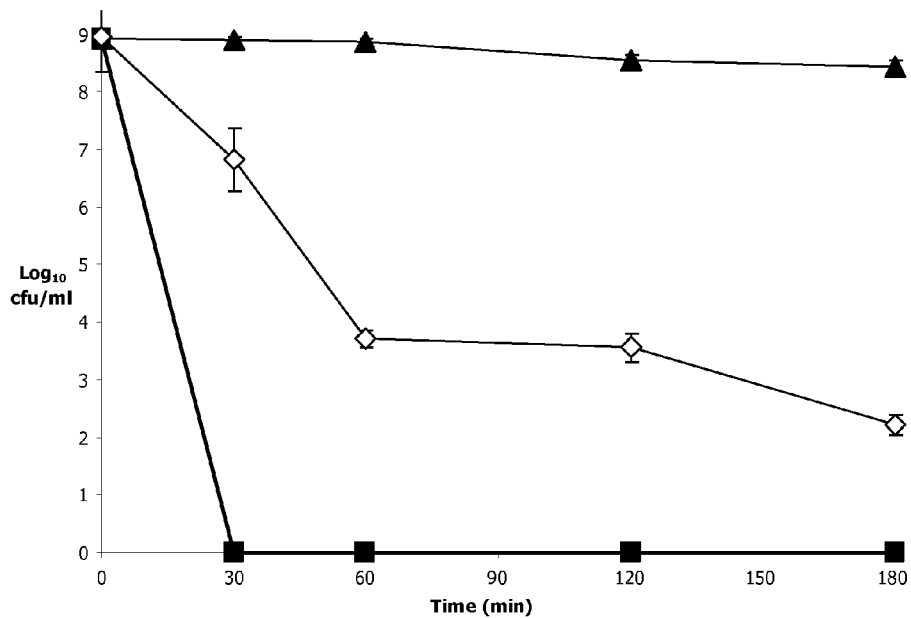
FIG. 9: Effect of microencapsulation on the survival of *Lb. rhamnosus* GG in ex vivo porcine gastric contents pH 2.0 at 37° C. ▲=Micro-beads pH 2.0; ◇=positive protein control pH 2; ■=Free cells pH 2.0.
Figure 10:
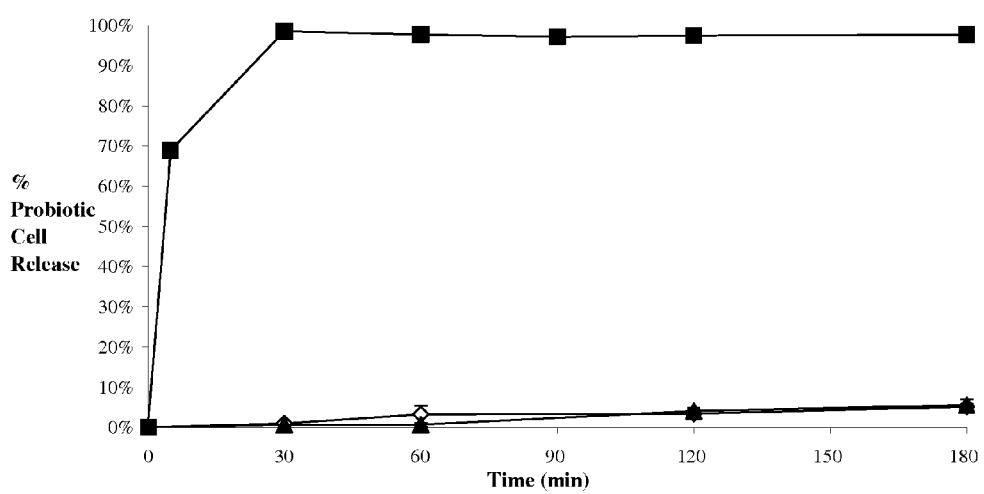
FIG. 10: Release of micro-encapsulated *Lb. rhamnosus* GG from whey protein micro-beads in ex vivo porcine gastrointestinal contents at 37° C. ◇=Micro-bead in gastric juice pH 2; ▲=Micro-beads in gastric juice pH 2.4; ■=Microbeads in small intestinal juice (jejunum) pH 6.6.
Figure 11:
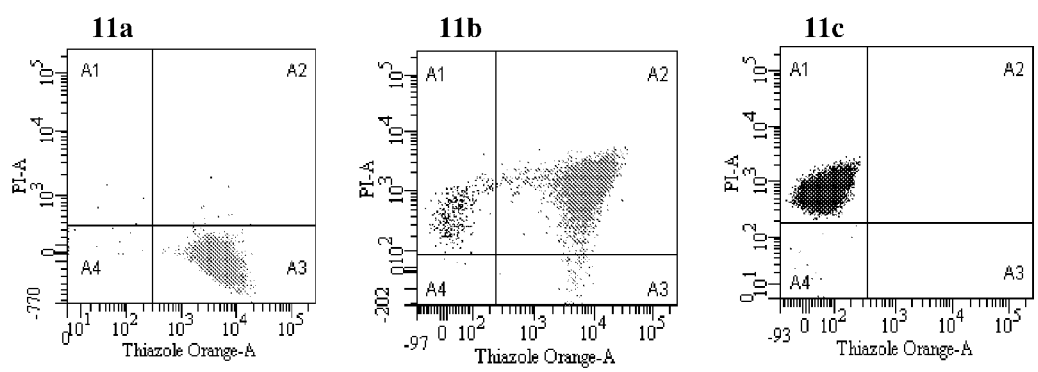
FIG. 11: Visualisation of cell viability in a) small intestinal juice following release of *Lb. rhamnosus* GG from whey protein micro-beads after gastric incubation (pH 2.0; 37° C.) and b) free cell control after 15 min and c) 3 h gastric incubation (pH 2.0; 37° C.). These flow cytometry dot plots illustrate live, injured and dead cells in quadrant A3, A2 and A1, respectively.
Figure 12:
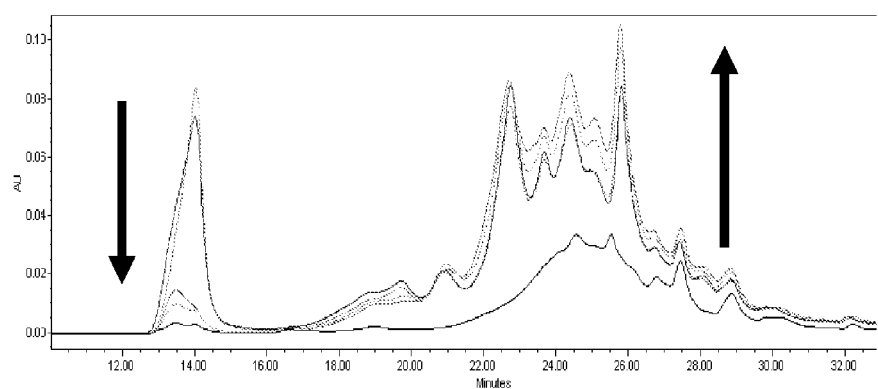
FIG. 12: Size exclusion chromatogram illustrating the gradual disintegration of whey protein micro-beads during incubation (0-180 minutes) in porcine intestinal contents pH 6.6 at 37° C. (150 rpm).
Figure 13:
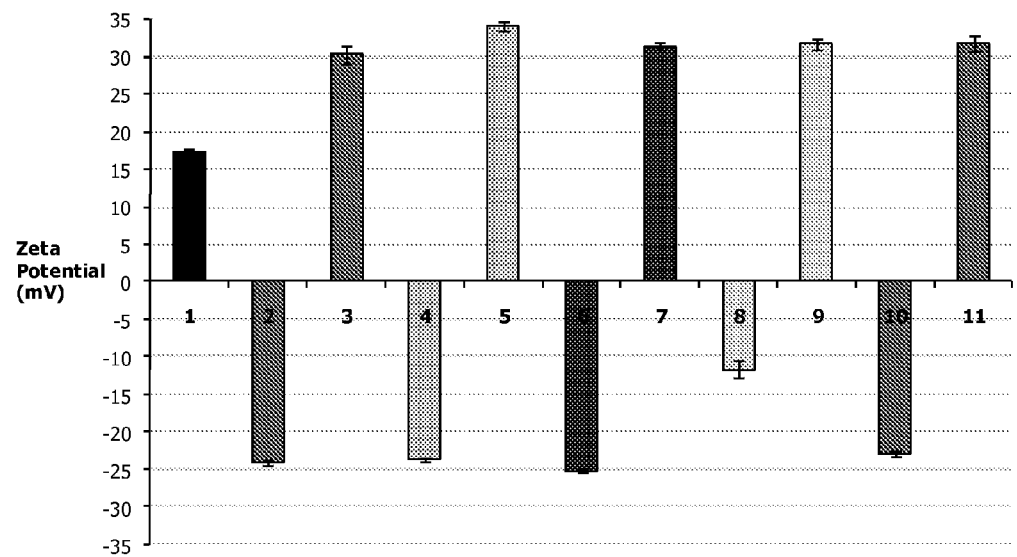
FIG. 13: Zeta potential of whey protein micro-beads mixture (uncoated=1) coated with anionic polysaccharides (2=apple pectin, 4=citrus pectin, 6=sodium alginate, 8=kappa carrageenan, 10=iota-carrageenan) and subsequently coated (double coating) with 1% (w/v) heat-treated WPI, pH 2.9 (3, 5, 7, 9 and 11). Error bars represent standard deviation of 3 independent tests performed in triplicate.
Figure 14:
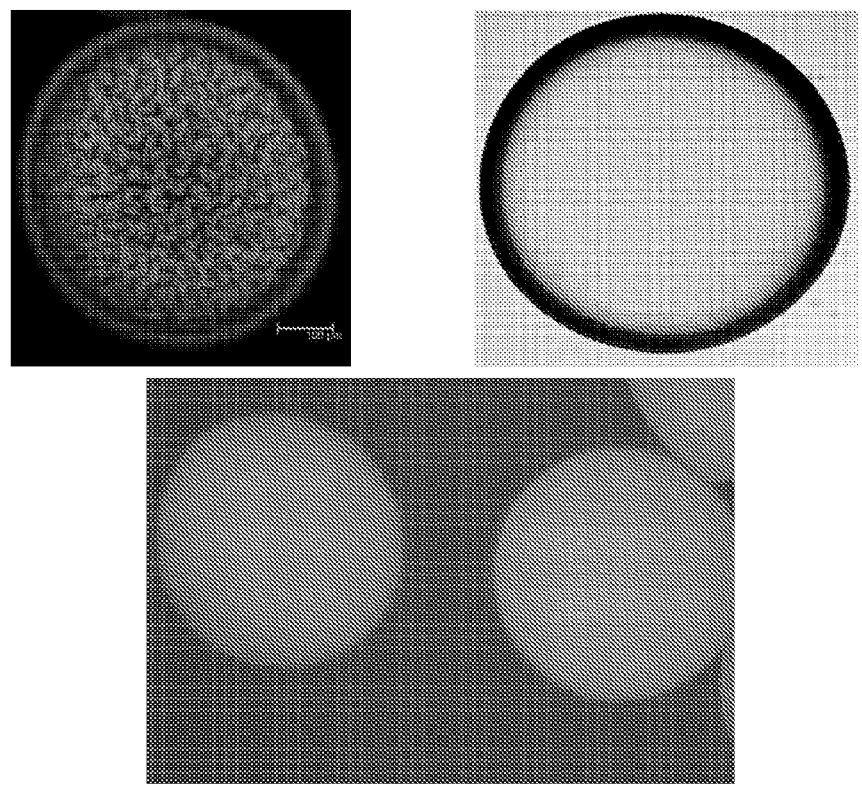
FIG. 14: Microscope images clearly differentiating between the micro-bead matrix and the polysaccharide coating layer.
Figure 15:
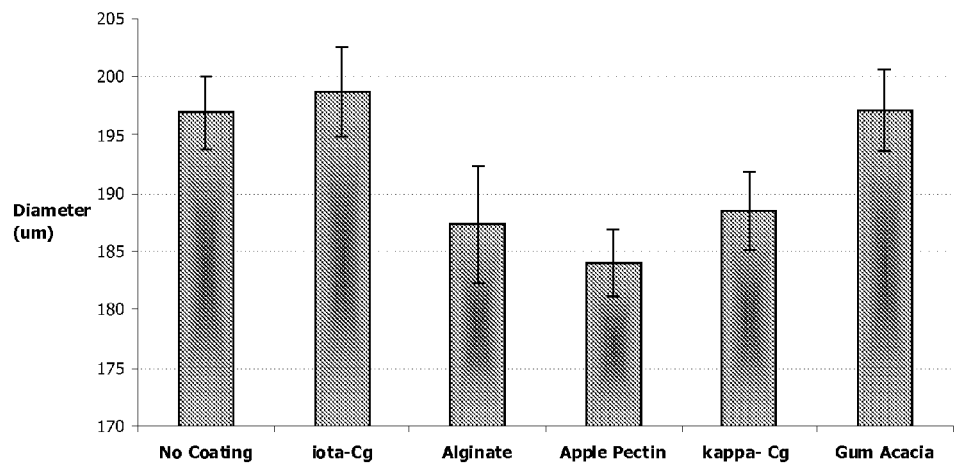
FIG. 15: Micro-bead diameter as a function of polysaccharide coating by means of layer-by-layer deposition.
Figure 16:
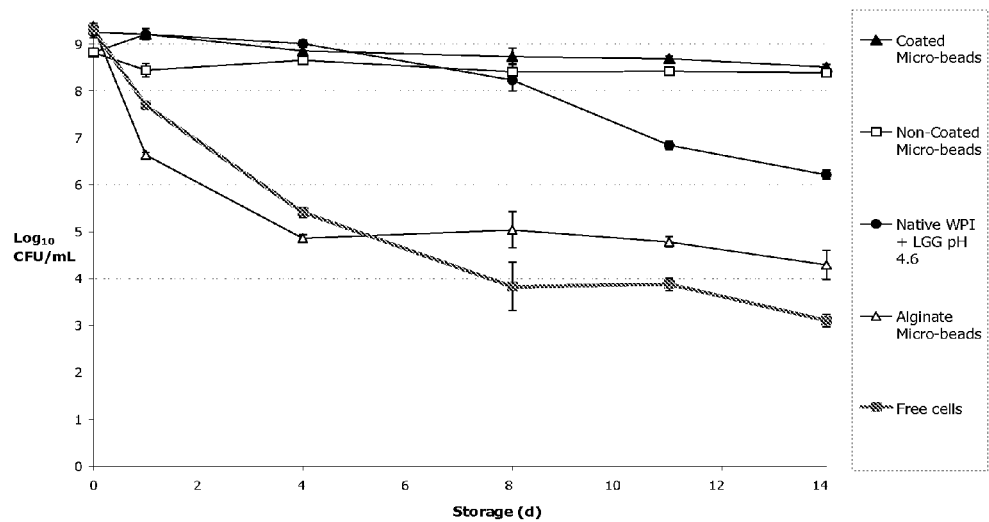
FIG. 16: Storage survival of coated and non-coated microbeads during 14-day storage at ambient temperature storage in cranberry juice (pH 2.6).
Figure 17:
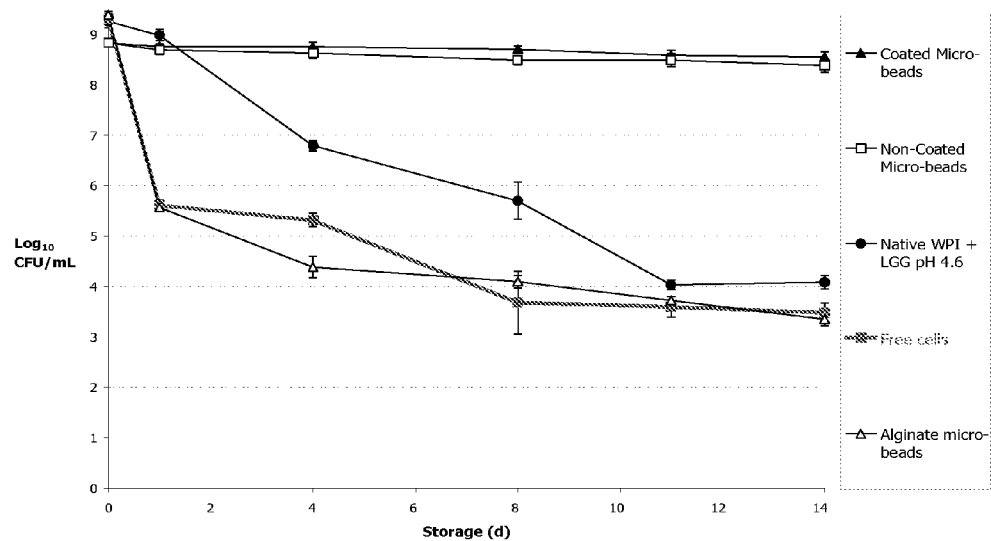
FIG. 17: Storage survival of coated and non-coated microbeads during 14-day storage during refrigerated storage (4° C.) in cranberry juice (pH 2.6).
Figure 18:
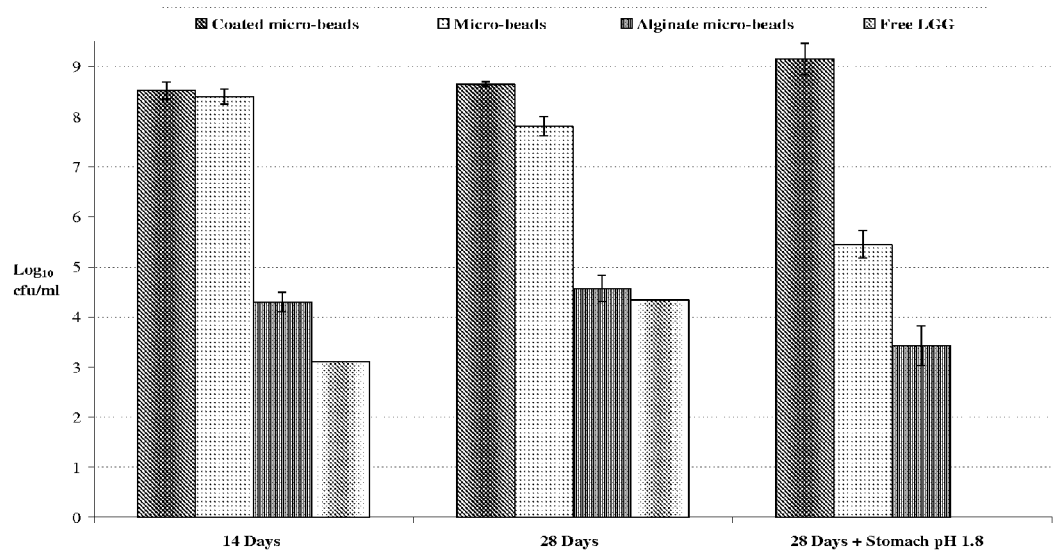
FIG. 18: Storage survival of coated and non-coated microbeads in cranberry juice (refrigeration temperature 4° C.) followed by ex vivo gastric incubation ph 1.8.

The curing media was formulated using an acetate buffer (0.5 M) adjusted to pH 4.6, where protein leakage was at a minimum value (see FIG. 3). This Following pH equilibration, 0.04-0.08% Tween-20 was added and the solution was subsequently filtered (0.22 μm), sterilized (121° C. for 15 minutes) and tempered at 35-37° C. prior to encapsulation experiment.

Production of Microbeads

Figure 1:
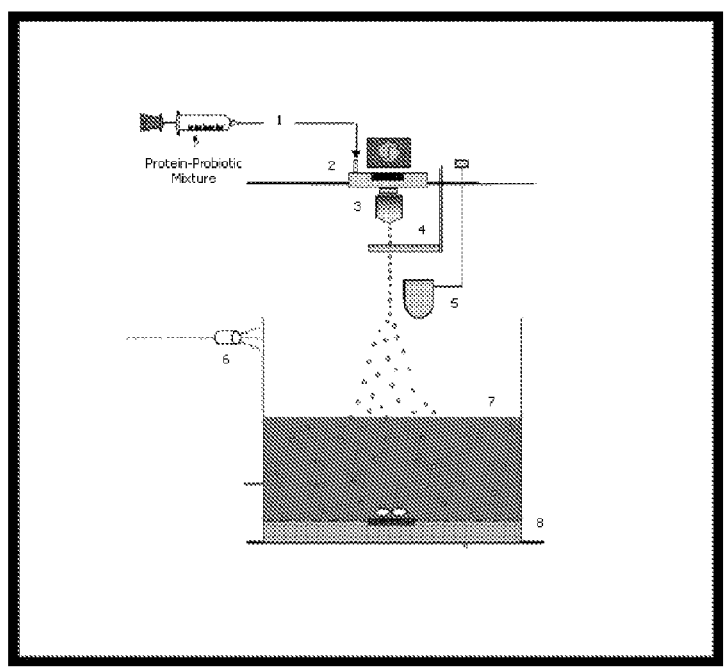
FIG. 1: Inotech® Encapsulator and the flow process during the extrusion procedure.
Figure 2:
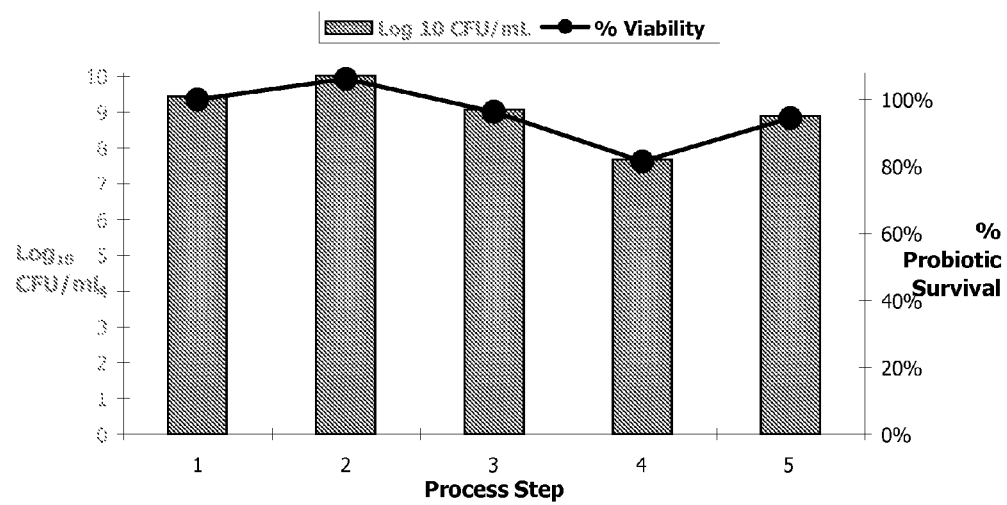
FIG. 2: Viability of probiotic cell population (*Lb. rhamnosus* GG) during the encapsulation procedure. 1=Fresh (19 hour) stationary phase cell suspension, 2=Homogenized cell suspension, 3=protein-probiotic mixture, 4=whey protein micro-beads, 5=Whey protein micro-bead+homogenization. *Lb. rhamnosus* GG yielded an extraction yield and encapsulation efficiency of 106.1±2% and 94.5±1.1%, respectively.

Monodisperse whey protein micro-beads were prepared using an encapsulation device (Inotech Encapsulator® Inotech AG, Dottikon, Swtizerland) illustrated in FIG. 1. The technology is based on laminar jet break-up induced by applying a sinusoidal frequency with defined amplitude to a nozzle (3). The protein-probiotic suspension is delivered to the nozzle via a feed line (1), which is connected to the polymer reservoir. Nozzles with diameters in the range 50-1,000 μm may be used. The nozzle is connected via a PTFE membrane, to a vibrating device (2), which is insulated from the surrounding structures by rubber mounts to avoid the generation of resonance frequencies in the system. The flow of polymer solution to the nozzle is accomplished using a precision syringe pump with maximum extrusion volume of 50 mL.

The production of <50 mL of micro-beads was sufficient to meet the requirements of this study; hence the encapsulator was utilized as a batch-reactor. All glassware and solutions used in the procedure were sterilized (121° C. for 15 minutes) and the protein suspension was equilibrated to room temperature, filtered sequentially through sterile 5-, 1.2-, 0.8- and 0.45-μm pore sized filters (Sartorious) and mixed thoroughly with the bacterial concentrate to yield a probiotic population corresponding to the stationary phase concentration ($10^9$ CFU/mL). The protein-probiotic blend was aseptically extruded through a 150-μm nozzle and subsequently passed through an electrode (4) into the encapsulation vessel (8) containing 250 mL of tempered (35° C.) curing buffer solution (7), with continuous agitation to avoid coalescence of micro-beads during polymerization. A collection cup, suspended (5) from the top plate, was utilized during the initial priming of the nozzle with protein-probiotic mixture. This facilitated the retrieval of initial polymer droplets with a diameter in excess of the predicted value (defined under controlled conditions) and thus ensured monodispersity of the subsequent micro-bead batch. The pliable micro-beads formed were cured for 3 hour at room temperature in order to guarantee complete protein polymerization. The resulting rigid micro-beads were recovered, washed twice in sterile water and subsequently analyzed.

The flow rate of the protein-probiotic suspension, vibrational frequency and vibrational amplitude were controlled as desired. The frequency may be estimated from knowledge of the physiochemical properties of the protein mixture for the chosen nozzle diameter; however in practice some adjustments were required to obtain a favorable micro-bead diameter. Consequently, the polymer mixture was delivered at a set feed rate to the nozzle to achieve a steady i) jet of liquid and ii) flow rate (3-10 mL/min), visualized with the aid of a stroboscopic device (6). An optimum vibrational frequency (900-3000 Hz) and amplitude (4.7 to 7) were defined thereafter to facilitate jet break-up and droplet production. Once these parameters were determined for a given protein-probiotic suspension, they were logged and utilized without adjustment for further batch production using identical polymer parameters.

Production of Polysaccharide Coated Microbeads

The following biopolymers were used as coating materials: Apple Pectin, Citrus Pectin, Sodium Alginate, Kappa carrageenan, iota carrageenan, and gum acacia. Pectin solutions were prepared in 10 mM phosphate buffer pH 7 while the remaining biopolymers were solubilized in distilled water. After complete dissolution, the pH was adjusted to 4.6. All treatment materials were filtered through 0.22 μm sterile filters. Each micro-bead preparation (prepared as above) was cured for max. 3 h, washed twice in sterile water and resuspended in 100 mL of the respective polysaccharide solution (pH 4.6). Micro-bead batches were agitated (100 rpm) overnight at room temperature and subsequently cured for 15 min in 0.2M $CaCl_2$. Double coating: Additional batches from each biopolymer treatment were washed and resuspended in heat-treated WPI (1% w/v: pH 2.9) and agitated under similar conditions.

Analytical Detection of Polysaccharide Coating

The electrophoretic mobility (EM) of coated whey protein micro-beads was determined using a Zetasizer (Malvern, Worcs., UK) following a homogenization (setting 3; 5 min) and centrifugation (5000×g; 5 min; 20° C.) procedure. EM was derived from the velocity of the protein-polysaccharide suspension under an applied electric field of 150 V and converted into zeta potential using the Helmholtz-Smoluchowski equation.

In-Vivo Data

The probiotic strain *Lactobacillus rhamnosus* GG (ATCC 53103, *Lb. rhamnosus* GG, Valio Ltd., Finland), was procured from University College Cork, under a restricted materials transfer agreement and harvested cells were stored as stock solutions in de Man Rogosa Sharpe (MRS) broth (Oxoid Ltd., Hampshire, U.K.) containing 50% (v/v) aqueous glycerol at −20° C. All tests were performed using subcultures from the same frozen stock, which was routinely checked for purity. The frozen culture was grown in MRS broth (Oxoid Ltd., Hampshire, U.K) at 37° C. under anaerobic conditions, achieved by activation of Anaerocult gas packs (Merck, Darmstadt, Germany). A spontaneous rifampicin-resistant ($LGG^{Rif}$) derivative, required to facilitate subsequent enumeration during the pig trial, was isolated by spread plating $10^9$ cfu's from an overnight culture onto MRS agar containing 100 μg of rifampicin/ml ($MRS^{Rif}$) (Sigma Chemical Co., Dorset, U.K). Following anaerobic incubation at 37° C. for 48 h, single colonies were selected and stocked in MRS broth containing 40% (v/v) glycerol. Pulsed-field gel electrophoresis was performed to ensure homology between band patterns of parent and variant strains of *Lb. rhamnosus* GG. Growth characteristics, heat and acid tolerance of both strains were also elucidated for further confirmation of strain similarity (data not shown).

Treatment Preparation (for In-Vivo Examples)

Prior to assay, $LGG^{Rif}$ was serially transferred three times in MRS broth (Oxoid Ltd., Hampshire, U.K.) and incubated anaerobically at 37° C. for 24 h (Merck, Darmstadt, Germany). Bacteria destined for encapsulation were propagated from 1% (v/v) inoculums for 19 h at 37° C. under anaerobic conditions. The probiotic biomass in early stationary phase ($10^9$ cfu/ml) was harvested by centrifugation at 5,200×g for 10 min at 4° C., washed, filter-sterilized and resuspended in sterile phosphate-buffered saline (Sigma Chemical Co., Dorset, U.K.). Fresh cells suspensions were homogenized and enumerated on MRS agar as described previously and subsequently blended with denatured whey protein to achieve a stationary-phase probiotic concentration ($10^9$ cfu/ml). This protein-probiotic blend was aseptically extruded through a 150-μm nozzle for large-scale production of micro-beads as described above. Micro-bead batches containing $1.7 \times 10^{10}$ cfu's, were polymerised, recovered and stored at 4° C. prior to animal dosing. Furthermore, coated micro-beads were prepared as described below by electrostatic deposition of apple pectin (Cybercolloids, Cork, Ireland) onto the surface of micro-beads following 2 h polymerization. A positive control was also prepared using a native (substrate) protein solution aseptically blended with the cell concentrate in order to attain consistent bacterial concentrations ($10^9$ cfu/ml) among all treatment samples. Bacterial populations were determined by homogenisation, dilution and pour-plating on MRS agar.

Determination of Probiotic Viability During Cranberry Juice Storage and Subsequent Gastric Incubation The viability and sensitivity of the encapsulated bacteria was evaluated within various coated micro-bead environments, by storing all treatments at room temperature and refrigerated conditions for 28 days. The enumeration of viable cells was conducted on days 0, 1, 4, 8 and 14 of storage. Entrapped bacteria were released from their respective protein network using a homogenization procedure (data not shown) to ensure complete liberation of bacteria from the respective protein systems. Planktonic *Lb. rhamnosus* GG cells (control) were treated similarly, to maintain consistent treatment conditions. Homogenates were spread-plated on MRS agar and colonies were subsequently counted after 48 h incubation at 37° C. under anaerobic conditions. Plates containing 30-300 colonies were enumerated and recorded as cfu/ml of protein material.

Probiotic Detection Using Flow Cytometry

In addition to plate counts, the viability of probiotic cells was assessed by flow cytometry (FACS), using the BD Cell Viability assay (BD Biosciences, Oxford, U.K.). Digesta homogenates were diluted to a pre-determined cell density and enzymatic treatment was performed in association with fluorescent staining. Data acquisition was performed on a BD FACS Canto II flow cytometer (BD Biosciences, Oxford, U.K.), equipped with 488 nm laser excitation and BD FACS Diva software using a side scatter (SSC) threshold.

Microscopy

Microscopy work was performed using a BX51 epifluorescence microscope and a Leica TCS SP5 confocal scanning laser microscope (CSLM) (Leica Microsystems, Wetzler, Germany) as described by Doherty et al.(2010). Briefly, gastro-intestinal contents were stained by integrating the dye concentrations previously optimized during FACS analysis and imaged using ×63 magnification objective with a numerical aperture of 1.4. Fluorescent and bright-field light microscopy were also performed on selected digesta sections using a BX51 light microscope (Olympus, Germany).

In-Vivo Transit Time Studies

Transit time of probiotic loaded micro-beads and sequential evolution of $LGG^{Rif}$ along the gastro-intestinal (GI) tract were investigated in vivo due to there consideration as fundamental pre-requisites for successful engineering of a full-scale animal trial. Feeding studies were performed with pigs, in compliance with European Union Council Directive 91/630/EEC (outlines minimum standards for the protection of pigs) and European Union Council Directive 98/58/EC (concerns the protection of animals kept for farming purposes) and were approved by, and a license obtained from, the Irish Department of Health and Children. Briefly, two weeks-post weaning, six male pigs were blocked by weight (mean weight of 13.2±0.6 kg), penned individually (as described below) and randomly assigned to two groups (n=3). Having fasted from the previous evening (16 h), both groups were dosed with protein micro-beads, loaded with $10^{10}$ cfu $LGG^{Rif}$, delivered by means of a highly palatable milk permeate (non-protein milk NPM) medium. Animals received 200 ml NPM post-probiotic administration. Two (n=3) and 3 h (n=3) later, animals were sacrificed by captive bolt stunning followed by exsanguination, in the same order as they were fed. Previous marker transit studies in pigs showed that the majority of ingested feed would have transited to the small intestine within 2 h; however sequential recovery of encapsulated probiotics may supersede these expectations due to the nature of the delivery system. Hence, data relating to the evolution of $LGG^{Rif}$ in the GI tract was elucidated by examining stomach and ileostomy contents of all treatment animals and microbiological analysis is documented below.

In-Vivo Pig-Feeding Trial

A total of 32 (male) pigs from different litters of a conventional crossbred program (Large White×Landrace) performed in Moorepark Pig Production Development Unit (MPDU), were weaned at c. 26 days of age. At 14 days post-weaning, (day −7) pigs were tagged, blocked by mean initial body weight (11.8±1.3 kg) and randomly assigned to one of four treatment groups (n=8): control, probiotic substrate suspension, probiotic micro-beads and coated micro-beads. Pigs were housed individually in pens designed to provide reasonable space for free movement and normal activity of pigs, thereby assuring normal GI motility (Snoeck et al., 2004). All pens, equipped with a single feeder and nipple drinker, were located in light-controlled (0700 h to 1630 h) rooms with temperatures maintained at 28-30° C. throughout the trial using a thermostatically controlled space heater. The next 7 days were documented as the acclimatisation period (day −7 to day 0), during which animals were fed a non-medicated commercial diet (free of antimicrobials, performance enhancers, and sweeteners) twice daily at 0730 and 1530 (350 g/serving) with ad libitum access to fresh water. During this period, animals were trained to consume a standard volume of carrier medium—pasteurized apple juice (Sgeez®, Dublin, Ireland)—within a defined time preceding their morning feed. Juice consumption, attitude of the animal and fecal consistency were monitored daily during the acclimatization period and were combined to generate a scoring system (data not shown). Any animals showing signs of ill-health were treated appropriately by on-site personnel. Animals had unrestricted access to water at all times during the study.

On day 0, fecal samples were taken 6 h after the morning feed for determination of baseline parameters. Freshly voided feces (5-10 g) were collected in sterile containers following rectal stimulation from two animals per treatment (n=8). Fecal samples were stored anaerobically at 4° C. and microbiological analysis was performed within 2 h as outlined below. In addition to the morning juice on day 0, all treatment groups were offered an extra juice serving as a replacement for the evening feed. Following an overnight fast (16 h), animals received probiotic treatments with their morning juice on day 1. The first group (A) received free $LGG^{Rif}$, which served as a control and the second group (B) was treated with native protein suspensions of $LGG^{Rif}$. Probiotic-loaded micro-beads were administered to the third group (C), while the remaining group (D) received polysaccharide coated micro-beads and no significant size difference existed between respective micro-bead treatments. A dosing method was optimized to mitigate animal stress during treatment administration, since animal handling retards GI transit time (Snoeck, et al., 2004). During probiotic administration, each pig received approx. 400 ml of apple juice containing c. $4.2 \times 10^7$ cfu/ml of $LGG^{Rif}$ in respective treatments, which provided a total dose of $1.7 \times 10^{10}$ cfu/animal. Use of a single carrier medium and standard micro-bead size are fundamental pre-requisites since fluctuating gastric transit times may result from variation in carrier viscosity and micro-bead size/density (Davis et al., 2001, Mpassi et al., 2001). Preliminary experiments (data not shown) revealed an encapsulation efficiency of 96.1%±0.7% for probiotic loaded micro-beads; thus control samples (group A and B) were adjusted to procure approximately equal $LGG^{Rif}$ concentrations among all treatment groups.

Two hours post-probiotic administration animals from treatment groups A, B and C were sacrificed (as described previously) while group D was randomized between two transit times (2 and 3 h) for the investigation of delayed cell release from coated systems. The entire GI tract was removed from each carcass immediately after slaughter and digesta (5-10 g) from various GI regions were aseptically collected. Gastric (pyloric) contents were sampled, after which intestinal digesta from a 1 m length of the jejunum was collected, beginning at a point 1 m distal from the pyloric valve. Digesta was also taken from a 1 m length of the ileum, starting at 15 cm proximal of the ileo-caecal junction, which was sequentially followed by collection of entire caecum contents. All samples were stored anaerobically and transported on ice to the laboratory where microbiological analysis was performed within 8 h of slaughter, as outlined below. Tissue samples were also collected during carcass dissection from stomach, jejunum and ileal regions described above. Small tissue specimens (1-2 cm) were immediately stored on ice for microscope and probiotic adhesion analysis; the latter being performed within 2 h of slaughter.

In-Vivo—Microbiological Analysis of Porcine GI Contents

Faecal samples were homogenised in Maximum Recovery Diluent (MRD) as 10-fold dilutions (w/w) using a stomacher (Lab-Blender 400; Seward Medical, London, U.K.); however all GI digesta were serially diluted using phosphate buffer (pH 7; 0.5 M) and homogenised in an ice bath to facilitate permanent inactivation of digestive enzymes and complete liberation of encapsulated bacteria. Appropriate dilutions were spread-plated on three media as described by Gardiner et al. (2004), for enumeration of $LGG^{Rif}$, total *lactobacilli* and *Enterobacteriaceae*. Briefly, probiotic counts for *Lb. rhamnosus* GG were obtained using MRS agar containing rifampicin (Sigma Chemical Co., Dorset, U.K.) as a selective agent and 50 U/mL of nystatin (Sigma Chemical Co., Dorset, U.K.) to inhibit yeasts and moulds after anaerobic incubation for 2 days at 37° C. ($MRS^{Rif}$). Fecal bacteria in the family of *Enterobacteriaceae* were enumerated on violet red bile glucose agar (Merck, Darmstadt, Germany) incubated at 27° C. for 24 h (VRBA), while total *Lactobacillus* counts were detected on *Lactobacillus*-selective agar (Rogosa et al., 1951) (Becton Dickinson, Cockeydville, Md.) following anaerobic incubation for 5 days (LBS). $LGG^{Rif}$ was easily identifiable on $MRS^{Rif}$ due to its distinct colony appearance i.e. well-developed, round, milky colonies however, randomly amplified polymorphic DNA PCR (RAPD-PCR) was performed (detailed below) to validate the presence of *Lb. rhamnosus* GG on $MRS^{Rif}$ plates. GI contents were analysed for pH determination (Mettler Toledo MP220 pH meter) within 6 h of slaughter.

In-Vivo—Adhesion Assay

Ileal tissue samples were rinsed gently in MRD to remove any loosely adhering digesta and were further washed by immersion in MRD and vigorous shaking for 60 s. Tissue samples were then homogenised in fresh MRD as 10-fold dilutions using a stomacher (Lab-Blender 400; Seward Medical, London, U.K.). The resultant homogenate was further diluted 10-fold in MRD and appropriate dilutions were plated on the three media detailed above for enumeration of adherent bacteria.

Anthocyanin Absorption by Microbeads in Fruit Juices 3.5 mg of micro-beads, prepared as described above, were mixed with 35 mL of commercial grape, pomegranate and cranberry juice in sterile 50 mL plastic tubes and stored horizontally in the dark for up to 13 days. Samples were taken every 24 hours. For sampling, the microbeads were allowed to settle for a minute before 2 mL of the juice sample was taken, centrifuged at 20,000×g for 5 minutes, its absorbance at 520 nm (indicative of anthocyanins) was measured and returned back to the stock sample of juice. Additionally the sample was scanned from 350 to 720 to detect any possible change in the absorption spectra. The pH was also verified prior each measurement.

Results

Figure 19:
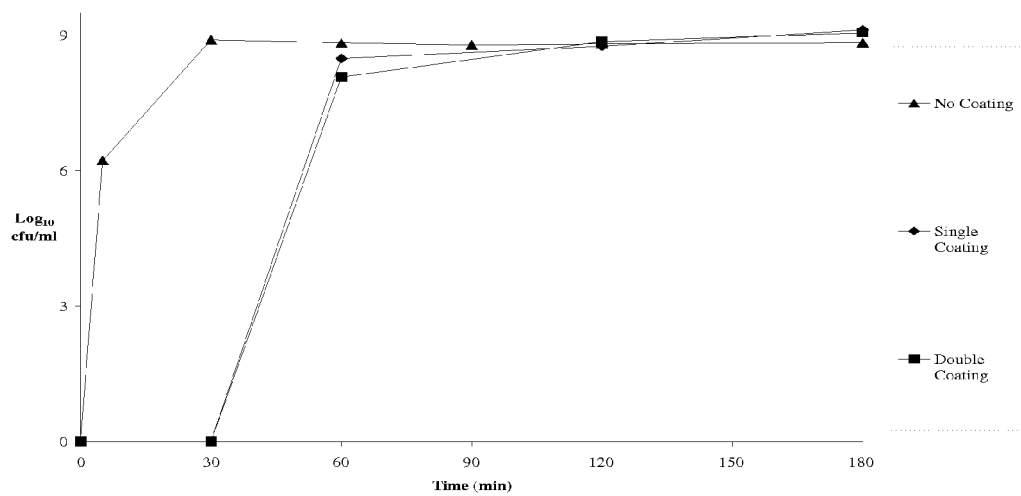
FIG. 19: Cell release from micro-beads during ex vivo intestinal incubation.
Figure 20:
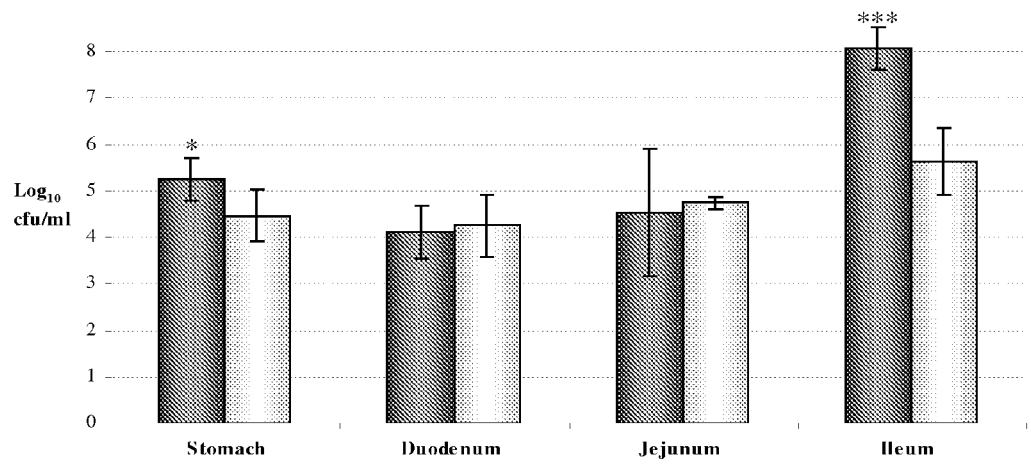
FIG. 20: Transit time of whey protein micro-beads as a function GI section 2-(▨) and 4-h (□) post probiotic administration. Data represents the mean values from 3 pigs (n=3 per treatment) with standard deviation of the means indicated by vertical bars. Asterisks denote significant differences (*$p<0.05$; *** $p<0.001$) in colony forming units 2 h post-probiotic administration relative to 4 h transition.
Figure 21:
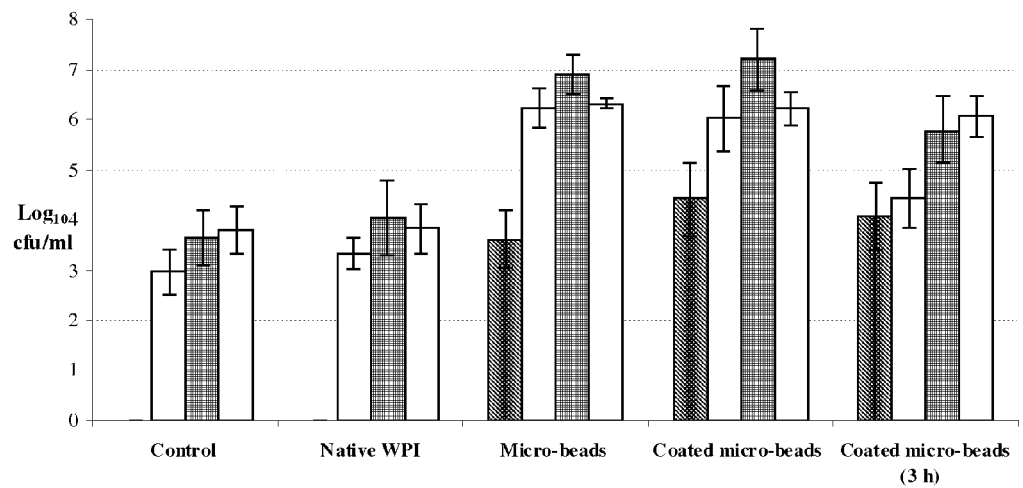
FIG. 21: Illustrates of the sequential evolution of LGG$^{Rif}$ survival within stomach (▨), jejunum (□), ileum (▨) and caecum (▨) post-probiotic administration as a function of treatment group.
Figure 22:
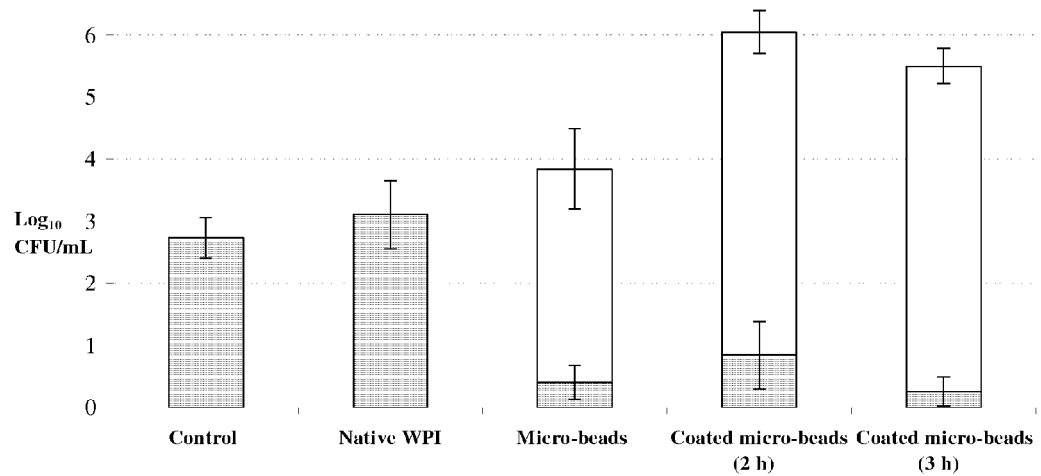
FIG. 22: Cell adhesion of LGG$^{Rif}$ (▨) and total *Lactobacillus* (□) to ileal tissue obtained 1 m proximal of the ileocaecal junction. The data represents the mean of value of two animals per treatment.
Figure 23:
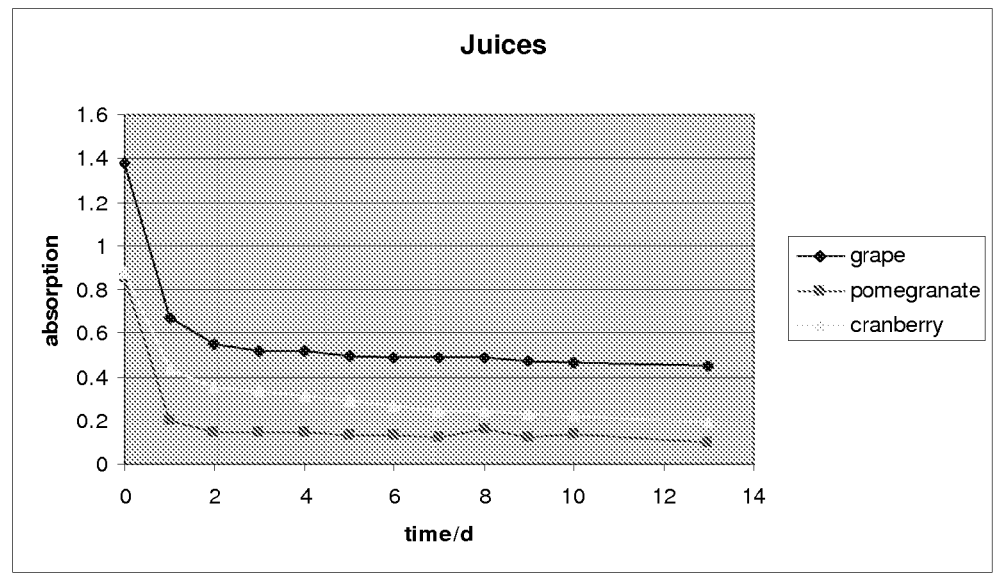
FIG. 23: Absorption at 520 nm of grape, pomegranate and cranberry juice in the presence of whey protein micro-beads at 4 degrees and storage for up to 13 days.

The data clearly indicated that microbeads according to the invention are capable of surviving passage through the stomach and rupturing to deliver the active agent in the lower intestine (see for example FIGS. 9 to 12). Ex-vivo data additionally indicates that coated microbeads are capable of delayed delivery to the small intestine, thus allowing distal intestinal delivery (i.e. delivery of the active agent in the ileum) (see for example FIG. 19). In-vivo data shows that the active agent, in this case probiotic bacteria, retain their functionality and viability upon delivery in the intestine. Referring particularly to FIG. 22, both uncoated and coated microbeads retain their ability to adhere to the ileal mucosa, that adhesion is improved by coating of the microbeads, and that adhesion persists for at least 3 hours.

The invention is not limited to the embodiments hereinbefore described which may be varied in construction and detail without departing from the spirit of the invention.

The invention claimed is:

1. A method for producing microbeads comprising an active component encapsulated within a gelled whey protein matrix, the method comprising the steps of providing a suspension of denatured whey protein and an active component, spraying the suspension through a vibrating nozzle to generate microbeads having an average diameter of from 80 to 500 µm, and immediately curing the microbeads by acidification by immersion in an acidic curing solution resulting in instantaneous gelation upon contact with the acidic curing solution, and wherein the denatured whey protein comprises denatured β-lactoglobulin.

2. A method as claimed in claim 1, wherein at least 90% of the microbeads have a diameter ranging from 80 to 500 µm.

3. A method as claimed in claim 1 in which the pH of the acidic curing solution is from 4.0 to 4.9.

4. A method as claimed in claim 1 in which the whey protein is a whey protein isolate.

5. A method as claimed in claim 1 in which the whey protein has a degree of denaturation of at least 90% w/w.

6. A method as claimed in claim 1 in which the whey protein suspension has a concentration of 5-15% w/w whey protein.

7. A method as claimed in claim 1 in which the acidic curing solution has an acid concentration of from 0.3M to 0.6M.

8. A method as claimed in claim 1 in which the temperature of the acidic solution is from 30° C. to 40° C.

9. A method as claimed in claim 1 in which the acidic curing solution comprises a surfactant to prevent or inhibit agglomeration of the microbeads.

10. A method as claimed in claim 1 in which the microbeads are subject to an extended curing period in the acidic curing solution, for a period of at least 15 minutes after gelation.

11. A method as claimed in claim 2 in which the whey protein has a β-lactoglobulin content of at least 30% w/w.

12. A method as claimed in claim 1 in which the whey protein suspension is sprayed through a vibrating nozzle and laminar break-up of the sprayed jet is induced by applying a sinusoidal frequency with defined amplitude to the nozzle.

13. A method as claimed in claim 1 in which the active component is a suspension of cells.

14. A method for producing coated microbeads comprising the steps of producing microbeads according to a method of claim 8, and resuspending the microbeads in a solution of anionic polysaccharide having a pH of 4.6 or less for a period of at least 60 minutes.

* * * * *